United States Patent
Lindberg

(10) Patent No.: US 10,863,909 B2
(45) Date of Patent: Dec. 15, 2020

(54) DEVICE AND SYSTEM FOR DETERMINING PHYSIOLOGICAL PARAMETERS FROM THE STERNUM BONE

(71) Applicant: Respiheart AB, Linkoping (SE)

(72) Inventor: Lars-Goran Lindberg, Linkoping (SE)

(73) Assignee: Respiheart AB, Linkoping (SE)

( * ) Notice: Subject to any disclaimer, the term of this patent is extended or adjusted under 35 U.S.C. 154(b) by 1063 days.

(21) Appl. No.: 15/308,526

(22) PCT Filed: May 4, 2015

(86) PCT No.: PCT/EP2015/059732
§ 371 (c)(1),
(2) Date: Nov. 2, 2016

(87) PCT Pub. No.: WO2015/166110
PCT Pub. Date: Nov. 5, 2015

(65) Prior Publication Data
US 2017/0055852 A1  Mar. 2, 2017

(30) Foreign Application Priority Data
May 2, 2014 (EP) .................................. 14166934

(51) Int. Cl.
*A61B 5/026* (2006.01)
*A61B 5/00* (2006.01)
(Continued)

(52) U.S. Cl.
CPC ........ *A61B 5/0261* (2013.01); *A61B 5/02055* (2013.01); *A61B 5/0295* (2013.01);
(Continued)

(58) Field of Classification Search
None
See application file for complete search history.

(56) References Cited

U.S. PATENT DOCUMENTS

2004/0225207 A1  11/2004  Bae
2007/0195330 A1   8/2007  Ohashi
(Continued)

FOREIGN PATENT DOCUMENTS

CN      102811657 A    12/2012
JP      2003508143 A    3/2003
(Continued)

OTHER PUBLICATIONS

Nitzan et al. "measurement of oxygen saturation in venous blood by dynamic near infrared spectroscopy", J. of Bio. Med. Opt. 2000.*
(Continued)

*Primary Examiner* — Amelie R Davis
*Assistant Examiner* — Marjan Saboktakin
(74) *Attorney, Agent, or Firm* — Olive Law Group, PLLC

(57) ABSTRACT

A system and method for determining at least one physiological parameter of a subject. The system comprises a sensor for skin apposition. The sensor comprises at least one light source for illuminating of a thoracic bone or a septum, and a detector for measuring of reflected and/or scattered light from blood vessels related to the thoracic bone or septum. The system further includes a control unit configured to control operation of the sensor and an analysing unit configured to analyse the measurement data for determining the at least one physiological parameter.

12 Claims, 12 Drawing Sheets

(51) Int. Cl.
| | |
|---|---|
| A61B 5/0295 | (2006.01) |
| A61B 5/1455 | (2006.01) |
| A61B 5/0205 | (2006.01) |
| A61B 5/024 | (2006.01) |
| A61B 5/08 | (2006.01) |

(52) U.S. Cl.
CPC .......... *A61B 5/1455* (2013.01); *A61B 5/6823* (2013.01); *A61B 5/6833* (2013.01); *A61B 5/02433* (2013.01); *A61B 5/0816* (2013.01); *A61B 2562/0238* (2013.01)

(56) References Cited

U.S. PATENT DOCUMENTS

| | | | | |
|---|---|---|---|---|
| 2011/0066059 | A1* | 3/2011 | Lehrman | A61B 5/725 600/529 |
| 2013/0060098 | A1* | 3/2013 | Thomsen | A61B 5/02028 600/301 |
| 2013/0261415 | A1 | 10/2013 | Ashe et al. | |
| 2013/0267854 | A1* | 10/2013 | Johnson | A61B 5/0082 600/473 |

FOREIGN PATENT DOCUMENTS

| | | | | |
|---|---|---|---|---|
| JP | 2007105329 | A | 4/2007 | |
| JP | 2008264302 | A | 11/2008 | |
| JP | 2010534083 | A | 11/2010 | |
| JP | 2013515528 | A | 5/2013 | |
| WO | 0117422 | A1 | 3/2001 | |
| WO | 2001017420 | A1 | 3/2001 | |
| WO | WO-200117421 | A1 * | 3/2001 | .......... A61B 5/6838 |
| WO | 2007097702 | A1 | 8/2007 | |

OTHER PUBLICATIONS

Schreiner, Collin et. al; "Blood Oxygen Level Measurement with a chest-based Pulse Oximetry Prototype System." Computers in Cardiology. Sep. 26, 2010. pp. 537-540. ISBN: 978-1-4244-7318-2.
International Search Report for International Application No. PCT/EP2015/059732, dated Jun. 5, 2015.
Written Opinion for International Application No. PCT/EP2015/059732, dated Jun. 5, 2015.
=First Office Action issued in counterpart Chinese Application No. 2015800221878 dated Oct. 31, 2018 (sixteen (16) pages).
Correspondence to European Patent Office in response to International Search Report and Written Opinion issued in counterpart European Application No. 15721206.9, dated Dec. 2, 2016 (ten (10) pages).
Communication from European Patent Office issued in counterpart European Application No. 15721206.9 dated Apr. 26, 2018 (six (6) pages).
Correspondence to European Patent Office in response to Communication issued in counterpart European Application No. 15721206.9 dated Oct. 26, 2018 (nine (9) pages).
Correspondence to European Patent Office in response to Communication issued in counterpart European Application No. 15721206.9 dated Oct. 29, 2018 (nine (9) pages).
Summons to attend oral proceedings and invitation to make written submissions from European Patent Office issued in counterpart European Application No. 15721206.9 on Apr. 10, 2019 (eight (8) pages).
Correspondence in response to summons to attend oral proceedings and invitation to make written submissions from European Patent Office submitted in counterpart European Application No. 15721206.9 on Aug. 23, 2019 (eight (8) pages).
Communication from European Patent Office issued in counterpart European Application No. 15721206.9 dated Oct. 14, 2019 (two (2) pages).
Communication of intent to grant from European Patent Office issued in counterpart European Application No. 15721206.9 dated Nov. 11, 2019 (forty-four (44) pages).
Decision to Grant European Patent from European Patent Office issued in counterpart European Application No. 15721206.9 dated Mar. 26, 2020 (two (2) pages).
Second Office Action issued in counterpart Chinese Application No. 2015800221878 dated Jun. 19, 2019 (six (6) pages).
English summary, dated Jul. 4, 2019, of Second Office Action issued in counterpart Chinese Application No. 2015800221878 dated Jun. 19, 2019 (six (6) pages).
Third Office Action issued in counterpart Chinese Application No. 2015800221878 dated Nov. 20, 2019 (nine (9) pages).
English summary, dated Nov. 27, 2019, of Third Office Action issued in counterpart Chinese Application No. 2015800221878 dated Nov. 20, 2019 (seven (7) pages).
Argumentation for response to Third Office Action issued in counterpart Chinese Application No. 2015800221878 dated Jan. 20, 2020 (twelve (12) pages).
Claims submitted in counterpart Chinese Application No. 2015800221878 on Feb. 5, 2020 (two (2) pages).
Response as filed to Third Office Action issued in counterpart Chinese Application No. 2015800221878 dated Feb. 5, 2020 (thirteen (13) pages).
English translation of Claims submitted in counterpart Chinese Application No. 2015800221878 on Feb. 5, 2020 (three (3) pages).
Hagblad, J. et al. "A technique based on laser Doppler flowmetry and photoplethysmography for simultaneously monitoring blood flow at different tissue depths." Med. Biol. Eng. Comput., 2010, 415-422, 48, Springer, Switzerland.
Decision of Refusal issued in counterpart Japanese Application No. 2017-508769 dated Jul. 29, 2019 (eleven (11) pages).
Notification of Reasons for Refusal issued in counterpart Japanese Application No. 2017-508769 dated Mar. 18, 2020 (two (2) pages).
English translation of Notification of Reasons for Refusal issued in counterpart Japanese Application No. 2017-508769 dated Mar. 18, 2020 (two (2) pages).
English translation of Amended Claims in response to Reasons for Refusal issued in counterpart Japanese Application No. 2017-508769 dated Mar. 23, 2020 (three (3) pages).
Amendment as filed in response to Reasons for Refusal issued in counterpart Japanese Application No. 2017-508769 dated Mar. 23, 2020 (six (6) pages).
English translation of Written Appeal as filed in response to Decision for Refusal issued in counterpart Japanese Application No. 2017-508769 dated Nov. 27, 2019 (nine (9) pages).
Written Appeal as filed in response to Decision for Refusal issued in counterpart Japanese Application No. 2017-508769 dated Nov. 27, 2019 (eleven (11) pages).

* cited by examiner

DEVICE AND SYSTEM FOR DETERMINING PHYSIOLOGICAL PARAMETERS FROM THE STERNUM BONE

CROSS REFERENCE TO RELATED APPLICATIONS

This application is a 35 USC 371 application of International PCT Patent Application No. PCT/EP2015/059732, filed on May 4, 2015, which claims priority to European Patent Application No. 14166934.1 filed May 2, 2014; all of the contents of which are hereby incorporated by reference herein in their entireties.

FIELD OF THE INVENTION

This invention pertains in general to the field of monitoring or determining physiological parameters from apposite a thoracic bone site, non-invasively. More particularly the invention relates to determining several respiratory parameters and centrally related cardiac parameters.

BACKGROUND OF THE INVENTION

It is known that in photoplethysmography (PPG) light from a light source, for example a light emitting diode (LED), is directed toward the skin and the light is absorbed, scattered and reflected in the tissue. A small amount of the reflected light is received by a photodetector (PD) placed adjacent to the LED (reflection mode) or at the opposite site of the LED (transmission mode). Variations in the PD signal are related to changes in blood flow and blood volume in the underlying tissue. It is generally accepted that the PPG signal can provide valuable information about the cardiovascular system. The PPG technique is used in a wide range of commercially available medical devices for measuring heart rate, oxygen saturation, blood pressure and peripheral blood circulation despite that the exact origin of the PPG signal is unknown.

Measuring on blood flow related deep tissue such as muscle tissue or bones has been disclosed in WO2007/097702. WO 2007/097702 discloses a method for the generation, detection and evaluation of a photoplethysmographic (PPG) signal to monitor blood characteristics in blood vessels of limited flexibility, such as in vascular compartments and vessels of deep tissues. Underlying the disclosure are the effects that the orientation and axial migration of red blood cells have on the absorption, scattering and reflection of light (photons) of near infrared and of blue-green wavelengths. In the disclosure, near-infrared wavelength light source(s) and blue-green-wavelength light source(s) are spaced at particular distances from a photodetector(s). This method allows continuous, non invasive monitoring of blood characteristics and changes in these characteristics over time. Data obtained by this method include blood pressure, blood flow, pulsatile blood volume and red blood cell velocity in blood vessels which are rigid or which have a limited flexibility, such as the vascular tissue of bone or in atherosclerotic or stiff vessels.

US 2013/0060098 discloses a monitoring device suitable for attachment on a surface of a subject, such as on top of the sternum. The device has a sensor for optical measurements based on photoplethysmography (PPG). Due to the optical geometry of the device it is only suitable to be used for measuring on soft tissue. The same is true for the device disclosed in "Blood Oxygen Level Measurement with a chest-based Pulse Oximetry Prototype System", C. Schreiner et al., Computing in Cardiology 2010; 37:537-540. Again the optical geometry of the device makes it only suitable to be used for measuring on soft tissue.

In ambulances and emergency clinics, a wide range of peripheral/separate devices and systems are used to measure vital physiological parameters related to heart function, respiratory function, blood pressure and temperature. This is cumbersome, time-consuming and expensive. Hence, there is a need of a single method, apparatus and system which may be used assessing, determining and/or monitoring most of the vital parameters in a simple to use and cost-effective way. Particularly using one sensor and without disturbing the respiratory tract of the patient, as it has been shown that many individuals, both healthy and patients may develop an incorrect breathing pattern. This dysfunctional respiration may be the start of a vicious circle in that way it gradually reduces the ability to exert oneself.

SUMMARY OF THE DISCLOSURE

Accordingly, examples of the present disclosure preferably seek to mitigate, alleviate or eliminate one or more deficiencies, disadvantages or issues in the art, such as the above-identified, singly or in any combination by providing a device, a system and a method, for optically measuring physiological parameters from bone tissue, according to the appended patent claims.

The new system makes it possible for monitoring from a new anatomical site, sternum or thoracic bone, thereby making use of the special anatomical architecture and blood flow regulation around the thorax and in the sternum bone. This makes it possible to monitor respiratory and cardiovasculatory parameters from only one optical sensor without disturbing the respiratory tract and offering centrally related cardiac measures such as heart rate, heart rate variability and also arterial oxygen saturation, $SaO_2$.

According to another aspect of the disclosure, a system for determining at least one physiological parameter of a subject is disclosed. The system includes a sensor for skin apposition; the sensor comprises at least one light source for illuminating of a thoracic bone or a septum, and a detector for measuring of reflected and/or scattered light from blood vessels related to the thoracic bone or the septum. The system further includes a control unit configured to control operation of the sensor and an analysing unit configured to analyse a vascular blood flow and/or volume characteristics of the measurement data from said blood vessels for determining the at least one physiological parameter.

The new instrumentation is an optical system which may be used for determining at least 10 different respiratory parameters and at least two cardiovasculatory parameters from only one sensor applied close to bone tissue, such as the sternum.

The disclosed system may especially be used to monitor respiratory related multiparameters from thorax and therefore provide a completely new tool for diagnosis, treatment and follow up of patients with dysfunctional respiration having COPD, asthma, fibro myalgia, sleep apnea, pain in neck-shoulder region, lower back pain.

Other respiratory related disabilities/diseases that may be monitored using the disclosed system are patients with rheumatic diseases such as rheumatid arthritis, spondylitis, systemic lupus erythematosus, inflammatory muscle diseases etc. Other diseases or disabilities where dysfunctional breathing often is a part are; furred animal allergy, pollen/ grass allergy, perfume oversensitivity, trauma, expectation performance, children with ADHD, sleep apnea, depression, anxiety attack etc.

The system may be used in emergency applications for simultaneous recording of 3 vital signs; heart rate, respiratory rate and oxygen saturation at the accident place, in connection with heart lung resuscitation (HLR), during transport in ambulance, helicopter or boat or in the emergency department. For example during shock and hypothermia there are different phases of respiratory rate (both tachypnea and bradypnea) as well as of heart rate (takycardia and bradycardia).

The non-invasive and wireless system may improve the quality of life for the individual by online monitoring of multiparameters and by optimizing diagnosis, treatment decisions and rehabilitation modalities.

In some examples of the disclosed system, the light source comprising at least one near-infra-red lights source and/or at least one red light source and/or a green light source. The different light sources may be used to measure different parameters. The red light source may be used to measure variation in oxyhemoglobin and/or deoxyhemoglobin with reference to a near infrared light source in the range 800 nm to 810 nm.

Additionally and/or alternatively, a near infrared light source with a wavelength in the range 900 nm to 950 nm may be used to measure variation in oxyhemoglobin and/or deoxyhemoglobin with reference to a near infrared light source in the range 800 nm to 810 nm.

Green light may be used to measuring the hemoglobin content with reference to a near infrared light source in the range 800 nm to 810 nm.

In some examples of the disclosed system, the wavelength of the lights sources may be in the range of 400 nm to 1200 nm, such as the red light source may have a wavelength between 640 nm to 680 nm, the near-infra-red light source may have a wavelength between 800 nm to 810 nm and/or between 900 nm to 950 nm. The green light source may have a wavelength between 540 nm to 590.

In some examples, the disclosed system further comprises a memory unit configured to store measurement data obtainable in operation of the sensor.

In some examples, the disclosed system also comprises a retention element adapted to hold the sensor at a skin site adjacent the thoracic bone or septum of the subject.

In some examples, the disclosed system is wirelessly connected to transfer the recorded information to a receiving unit.

In some examples, the receiving unit may be connected to the control unit and/or the analysing unit In some examples of the disclosed system, the retention element is a skin adhesive member.

In some examples of the disclosed system, the vascular blood flow and/or volume is arterial blood flow and/or volume.

In some examples of the disclosed system, the at least one lights source and the at least one detector is arranged in a double lining configuration covering vessels emerging from left and right internal thoracic arteries and its corresponding collecting veins, and wherein the length of said sensor correlates to the volume of blood covered during a measurement.

This configuration is used to cover vessels emerging from left and right internal thoracic arteries and its corresponding collecting veins. This configuration will improve the signal to noise of the measured data.

In some examples of the disclosed system, the analysing unit is configured to detect oxygen saturation based on a quotient between the red light and the near infrared light and/or between two near infrared lights with different wavelengths. The analysing unit may also be configured to detect haemoglobin content based on a quotient between the green light and the near infrared light which is used as a reference.

In some further aspects of the disclosure, a method for non-invasively determining at least one physiological parameter based on a vascular blood flow and/or volume characteristics related to a thoracic bone or a sternum of a subject is disclosed. The method comprising, providing a sensor including at least one light source and/or at least one detector adapted to be arranged at a skin site of the thoracic bone or the septum of the subject. The method may further include transmitting light from the at least one light source to the thoracic bone or septum and detecting at least part of the transmitted light being reflected and/or scattered by blood vessels related to the thoracic bone or septum. The method may also include analysing and evaluating the reflected and/or scattered light detected by the at least one detector for determining the at least one physiological parameter.

In some examples, the disclosed method includes assessing blood flow in rigid vessels or in vessels of limited flexibility.

In some examples of the disclosed system, the analysing and evaluation is assessed from the blood flow supply anatomy of the sternum, wherein the blood flow to sternum varies synchronously with the blood flow supply to other parts of sternum.

In some examples of the disclosed system, the at least one physiological parameters are any of Respiratory Rate, Inspiration time, Expiration time, respiratory efficiency during normal effort, respiratory efficiency during maximal effort, Inspiratory reserve, Expiratory reserve, Inspiration coefficient, Expiration coefficient, heart rate (beats/min), Respiratory curve or pattern, oxygen saturation SaO2(%), hemoglobin content or temperature.

In some examples of the disclosed system, the parameters are monitored in real-time.

In some examples of the disclosed system, the vascular blood flow and/or volume is an arterial blood flow and/or volume.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EXAMPLES

Figure 1:
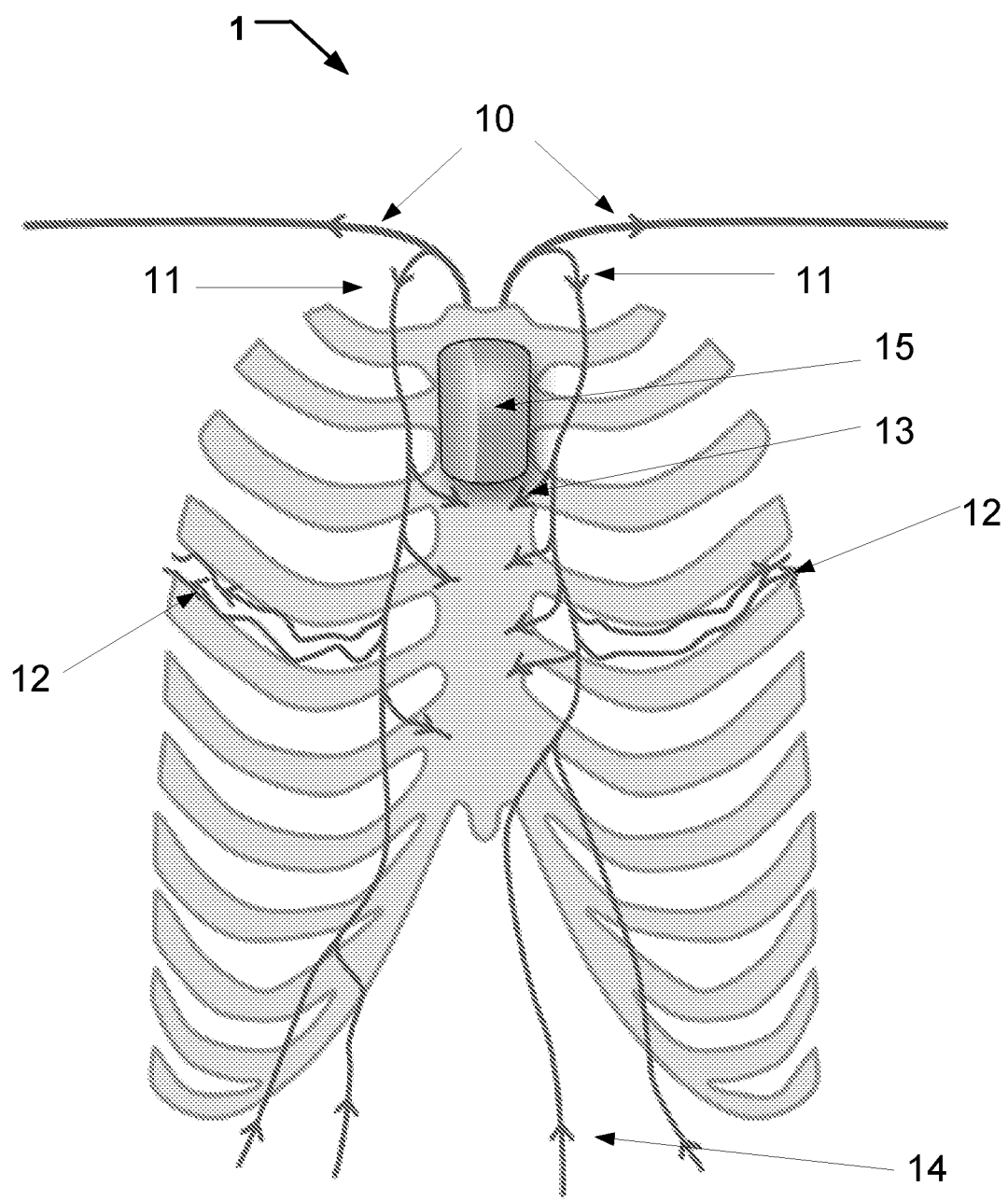
FIG. 1 is illustrating a schematic overview of blood flow to thoracic bone and sternum.

Specific examples of the disclosure now will be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure applicable to a device and method for determining physiological parameters from measured or monitored blood flow characteristic related to thoracic bone and in particular to a location apposition to sternum. However, it will be appreciated that the disclosure is not limited to this application but may be applied to many other locations viable for assessing, monitoring and/or measuring blood flow characteristics in rigid vessels or in vessels of limited flexibility.

FIG. 1 is illustrating a schematic overview of blood flow around the thorax and in the sternum bone 1. Research has shown that thoracic bone, and in particular sternum bone, has a special function related to the vessel architecture and physiology around the thorax. The internal thoracic artery 11, which branches off from the subclavian artery 10, and the corresponding collecting veins has branches to both the intercostal muscles 12 and to the sternum 13. The intercostal muscles 12 assist in respiration. In addition, there are arteries from the lower part of the body 14 that both branches to the abdominal muscles and join the internal thoracic artery and corresponding veins in terms of collaterals. The branches to the abdominal muscles assist in respiration. This means that the blood flow to the sternum may easily be modulated by; a) the pressure changes in the thoracic cavity synchronously with respiration and b) blood circulation related to the activity of the thoracal and abdominal muscle compartments, especially during forced respiratory activity.

Additionally, blood flow in the sternum is also modulated by the steady and pulsatile blood flow synchronous with the beating heart activity. As the sternum bone is the place for blood cell production (in the red bone marrow) it is highly perfused with blood but without any special nutrional or metabolic demand for blood.

The inventors have found that measurement of blood flow in the highly perfused sternum bone using a sensor 15 positioned apposition thoracic bone or sternum 1 enable monitoring of both respiratory and cardiac activity of several features and vital parameters.

The placement of a sensor 15 directly on the sternum also makes it possible to follow the overall respiratory pattern without disturbing the respiratory tract (as for a spirometer which introduces a respiratory resistance being inappropriate for patients with COPD, asthma etc.).

The placement of a sensor 15 directly on the sternum also means that the measured blood flow variations corresponding to the heart activity is of more central origin due to the relatively short distance between the heart and the position of the sensor.

FIG. 1 illustrates one example of the position of a sensor 15 on the sternum using only one unit including both a control unit and the sensor. Other positions of the sensor 15 on the ribs and a thoracic bone may also be plausible.

Figure 2:
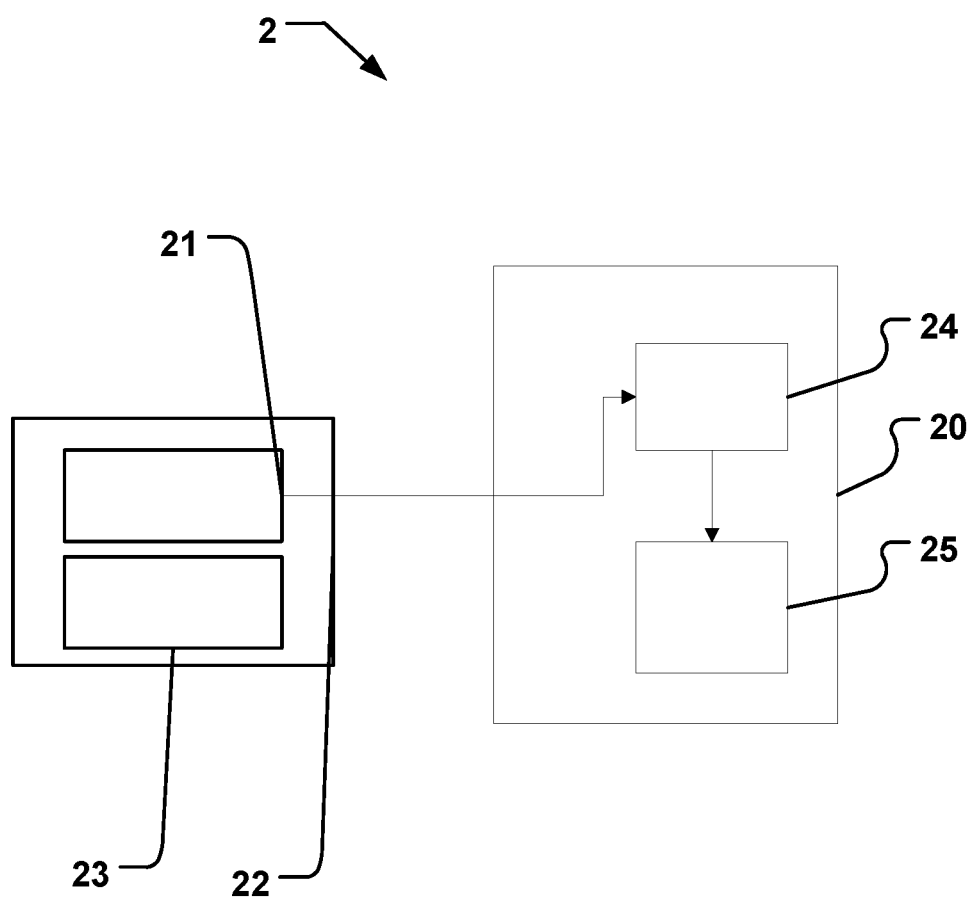
FIG. 2 is illustrating a schematic illustration of an example of a sensor system in accordance with the disclosure.

FIG. 2 is illustrating a schematic example of a sensor system 2 in accordance with the disclosure. The sensor system 2 is a medical system for determining at least one physiological parameter based on a blood flow, such as vascular blood flow, and/or volume characteristics related to a thoracic bone or around the thorax and in the sternum bone of a subject. The sensor system 2 comprises a sensor 22 for skin apposition. The sensor 22 comprises at least one light source 21 for illuminating of the thoracic bone or septum and at least one detector 23 for detecting and recording reflected and/or scattered light from vessels in or around the thoracic bone, or in the septum. The light sources 21 may preferably be at least one near-infra-red light source and/or at least one red light source and/or at least one light source between violent to green. An example of a light source that is due to its small size is suitable to be used in the sensor 22 is LEDs, such as near-infra-red LEDs or Red LEDs or violent to green LEDs.

Wavelengths in the range of 400 nm to 1200 nm, such as wavelengths in the range 540 nm to 950 nm, may be used to measure blood flow variations in the sternum bone. The wavelength used depends on the parameters to be measure. For example, a light source with a wavelength around 800 nm to 810 nm may be used as a reference, since variation in oxygen level in the blood may not be detected using this wavelength range. To detect oxygen saturation, light sources using either a wavelength in the range of 640 nm to 680 nm for oxyhemoglobin and/or deoxyhemoglobin, such as around 660 nm, and/or a wavelength between 900 nm to 950 nm for oxyhemoglobin and/or deoxyhemoglobin, such as around 940 nm, may be used. By measure light reflection and/or scattered using these ranges the blood oxygen saturation $SaO_2$ (%) in the sternum bone may be detected. The detection is based on an algorithm that differs from the ones used in commercially available pulse oximeters. The oxygen content may be determined by a quotient between total (DC) light reflection and/or scattered of two wavelengths, for example near infrared in the range 800 nm to 810 nm and red light in the range 640 nm to 680 nm. Additionally and/or alternatively, for some examples, the oxygen content may be determined by a quotient between total (DC) light reflection and/or scattered of two wavelengths in the range 900 nm to 950 nm and 800 nm to 810 nm. These quotients have empirically been found to correspond to oxygen saturation in blood samples whereas oxygen saturation was measured at a chemical lab using standard lab methods. Due to total light reflection and/or scattering and the highly perfused sternum bone with steady metabolic need the determined oxygen saturation is assumed to be of arterial origin, which is denoted as $SaO_2$.

To determine the content of hemoglobin it has been discovered that using a light source having a wavelength in the violent to green range, such as between 400 nm to 590 nm, such as a green light source with a wavelength between 540 nm to 590 nm, such as about 560 nm, it is possible to detect a light reflection and/or scattering signal from the vessels in the sternum bone. Normally, no reflected and/or scattered light will be detected from tissue in this wavelength range as the absorption is very high. The hemoglobin content may be determined by a quotient between total (DC) light reflection and/or scattered of two wavelengths, for example near infrared in the range 800 nm to 810 nm and green light in the range 540 nm to 590 nm.

Alternatively, in some examples, the sensor 21 may be a photoplethysmography (PPG) type of sensor.

The sensor system 2 further comprises a control unit 20 connected to the sensor 22 and configured to control operation of the sensor system 2. The sensor 22 and the control unit may be connected by wire or wireless using, for example Bluetooth.

The control unit 20 either includes an analysing unit 25 or is connected to an analysing unit 25. The analysing unit 25 is configured to analyse measured data from the detected and recorded light to obtain at least one physiological parameter.

It is not needed for the analysis to be performed at the site of the subject carrying the sensor. Neither is it needed for the analysis to be performed simultaneously as the measurements. The analysis may, for example, be performed later when needed.

On the other hand, in some example, the analysis may be done simultaneously, i.e. in real-time, as the measurements are performed.

In some examples, the sensory system is wirelessly connectable to transfer the recorded information to a receiving unit. The receiving unit is connected to either the control unit and/or said analysing unit. The Additionally, in some examples the control unit 20 includes or is connected to a memory unit 24 configured to store measured data from the detected and recorded light obtainable from the sensor 22 when operating the sensor system 2.

Additionally, in some examples sensor system 2 further comprises a unit for plotting a respiratory power curve based on the measured reflected and/or scattered light.

The sensor 22 may, in some examples, be attached to the skin using a special interface set-up/connection between the sensor 22 and the skin. This interface may be double adhesive tape, adhesive spray, skin glue, jelly, soft material engorging the sensor 22 and/or negative pressure.

Alternatively, in some examples, the sensor 22 may also be attached to the skin as being part of a textile wearable material, such as bra, T-shirt, shirt, undershirt etc.

Additionally, in some examples, the system may be combined with a second system developed to measure the blood pressure from soft tissue. The second system may provide the blood pressure measurement from the ankle of the arm wrist. One example of such a sensor system for measuring systolic blood pressure is disclosed in WO 2006/049571. The disclosed method and means for measuring the systolic blood pressure is hereby incorporated in its entirety. The incorporated disclosure relates to the disclosed flexible pad for measuring systolic ankle blood pressure. The pad comprises two or more pairs of light emitting diodes and photo detectors. The pairs being disposed in parallel and the detectors being adapted for detecting light emitted by the respective diode into tissue and reflected and/or scattered from there. The pad further includes conductor means for providing power to the light emitting diodes from a power source and means selected from conducting means and wireless means for putting the detectors in communication with electronic equipment for detector signal analysis.

The pads may be included in a system, wherein the system comprises an inflatable cuff, pump means for inflating and deflating the cuff. The system may further include gauge means for recording the pressure in the cuff as well as electronic means for amplification of photodetector signals.

The incorporated part of the disclosure also relates to the method for measuring systolic blood pressure of a subject. The method comprising providing an assembly including an inflatable cuff, a flexible measuring pad comprising two pairs or more of light emitting diodes and photo detectors, and an electronic control unit in communication with the pad. Positioning the pad or a combination of pad and cuff, in contact with the skin of an ankle or wrist region of the subject so as to dispose one pair in proximity of the anterior tibial artery and substantially parallel with it and the other pair in proximity of the posterior tibial artery and substantially parallel with it. The method den includes, inflating the cuff to a pressure sufficient for stopping blood flow through the anterior and posterior tibial arteries. After inflating the cuff the following steps are performed:

deflating the cuff while making the diodes emit light;

recording the light reflected and/or scattered from the tissue by the photo detectors during deflation;

recording the cuff pressure during deflation;

analysing the recorded light signal to identify the cuff pressure at which of blood flow in the anterior and/or posterior tibial arteries is resumed.

Figure 3:
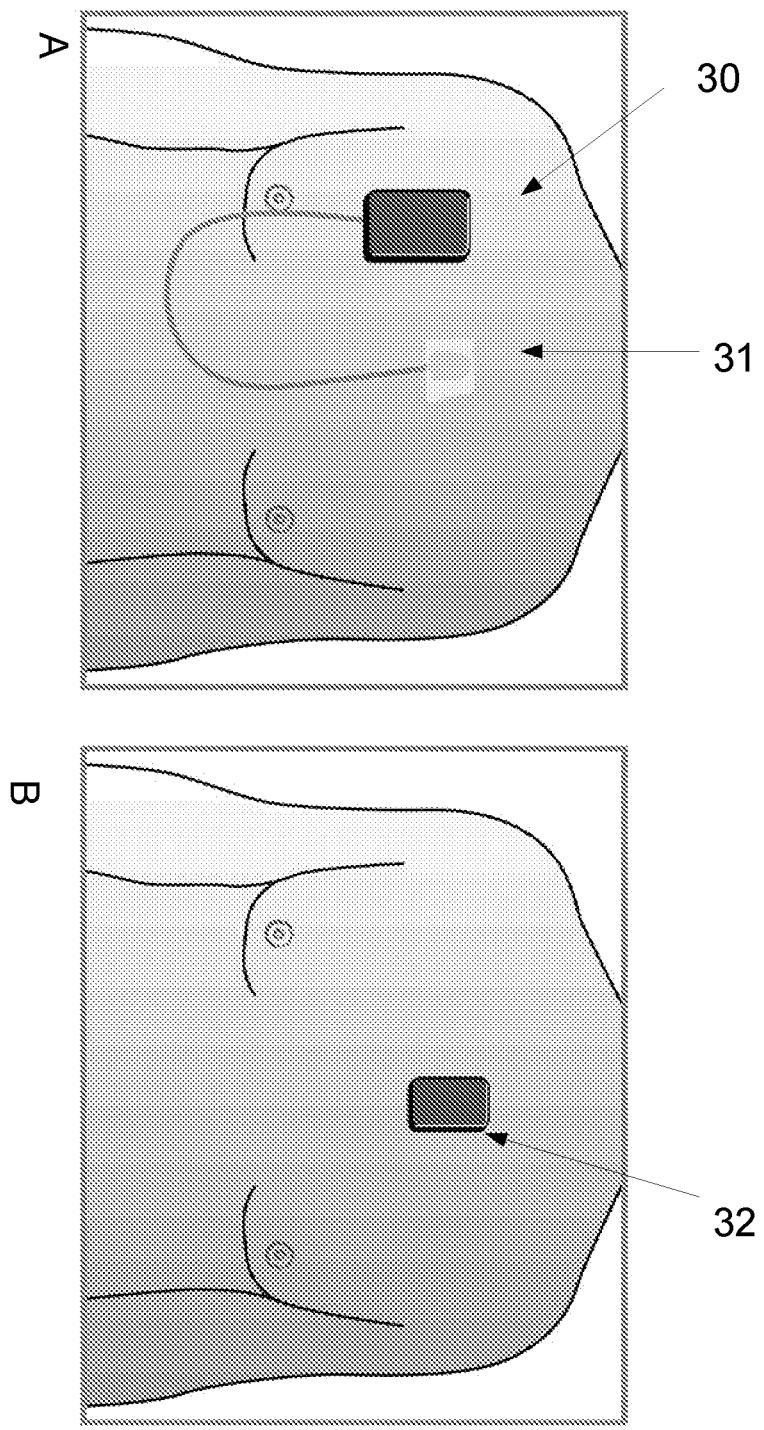
FIG. 3 is illustrating examples of devices in accordance with the disclosure and positions at a skin site apposition to a thoracic bone or sternum.

FIG. 3 illustrates two examples of the sensor system positioned at thoracic bone or sternum. In the illustrated examples the sensor system is positioned at the sternum.

In these examples the sensor systems comprise a control unit and a sensor configured to use wireless technology to communicate with a receiving unit for transferring of recorded data to and/or from the control unit. The receiving unit may be a computer, reading plate, mobile phone, or other communication platforms for transferring information of the subject to a hospital, a medical practitioner or to a nurse.

In example A of FIG. 3, the sensor 31 is positioned at a position on the thoracic bone, preferably at sternum. The control unit 30 may be positioned in a breast-pocket of a shirt, T-shirt or other clothes or at a trousers belt or at a skin surface close to the subject. The sensor 31 is separately attached to the skin. The sensor used may be in some examples be a photoplethysmography (PPG) type of sensor. In the illustrated example, the sensor 31 and the control unit 30 may be connected using a wire. Alternatively the sensor 31 and the control unit may be connected using wireless technology.

In example B of FIG. 3, the sensor and the control unit are integrated into one device 32.

Additionally, in some examples of configurations, both the sensor system of example A and example B may be equipped with a display on the control unit. The display may be configured to present data, such as vital parameters, directly on the control unit.

Figure 4:
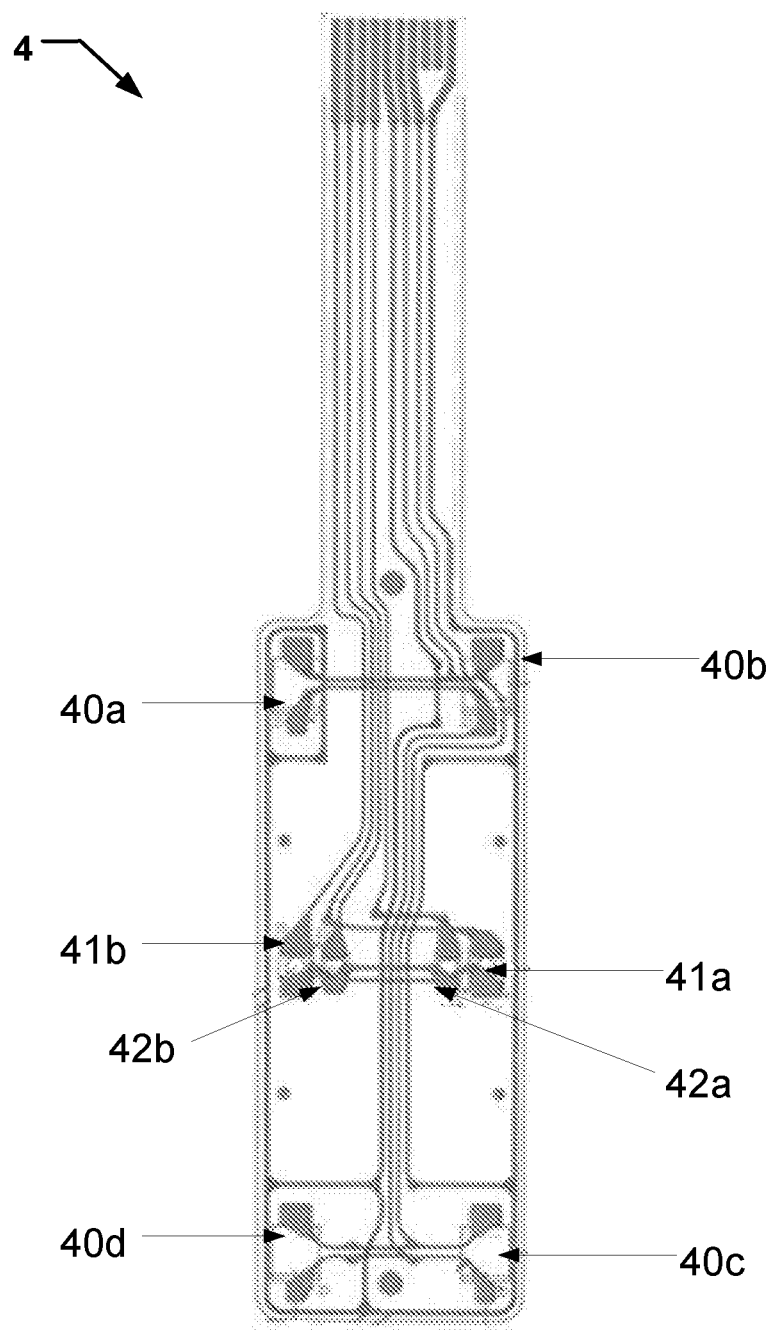
FIG. 4 is illustrating an example of sensor configuration with leads.

FIG. 4 illustrates an example of a sensor configuration 4 as a printed circuit card. The illustrated example comprises connecting leads and a double lining of LEDs 41*a-b*, 42*a-b* and photodetectors 40*a-d*. In this example of a sensor configuration 4 illustrated in FIG. 4, the LEDS may be Near-infra-Red LEDs, 41*a-b* and Red LEDs 42*a-b*.

The optical geometry of the lights-sources and detectors are arranged so that the light can penetrated and reach the vessels in and/or around the thoracic bone, or in the septum bone.

The double lining configuration is preferred to cover vessels emerging from left and right internal thoracic arteries (see FIG. 1) and its corresponding collecting veins. The length of the sensor may correlate to the volume of blood covered during measurement. Both these factors may enable a big blood volume to be recorded which enhances the strength of the PPG signal and therefore signal to noise ratio (SNR).

In more general term, the arrangement of the lights sources and the photodetectors of the sensor should preferably cover the length and from left to right of the thoracic bone or septum, thereby provide a large measure area covering as many of the blood vessels, in and around the thoracic bone or septum as possible.

Alternatively, other configurations of the LEDs and photodetectors are possible, such as a configuration including at least one near-infra-red LED, such as a LED having a wavelength between 800 nm to 810 nm, in combination with at least one red LED, such as a LED having a wavelength between 640 to 680 nm.

Alternatively and/or additionally, in some examples, the configuration may include at least two near infrared light LEDs, such as at least one having a wavelength between 800 nm to 810 nm and at least one having a wavelength of between 900 nm and 950 nm.

Alternatively and/or additionally, in some examples, the configuration may include at least one LED having a wavelength between 400 nm to 590 nm, such as 550 to 590 nm.

The configuration mainly depends on the anatomy of the location of the thoracic bone and the vital parameters to be measured.

Additionally, in some examples, the printed card of the sensor 4 is casted in hard or partly flexible silicone, acrylic or other material moulded with a special geometry to be adapted to the anatomical appearance over the sternum, such as the anatomical appearance of both males and females.

Figure 5:
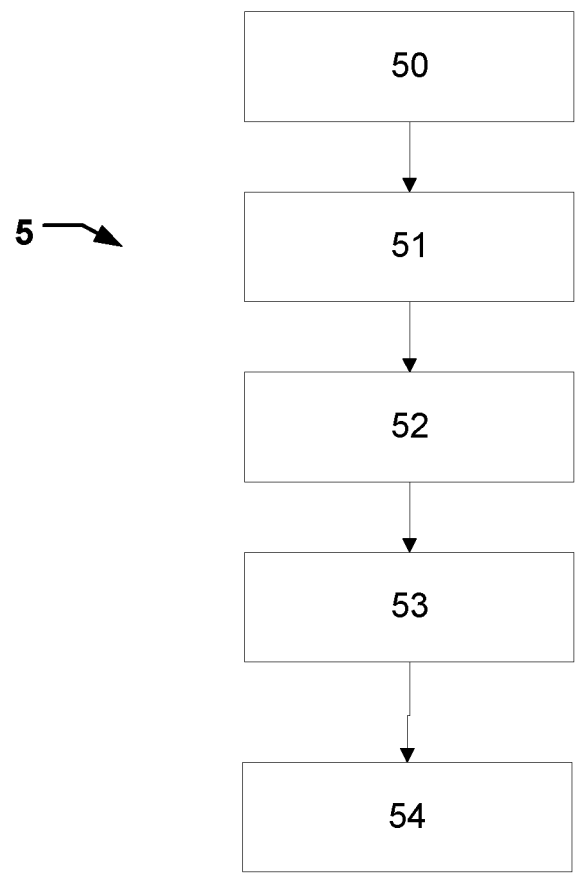
FIG. 5 is illustrating schematic overview of an exemplary method in accordance with the disclosure.

FIG. 5 is illustrating schematic overview of an exemplary method 5. The method is for non-invasively determining at least one physiological parameter based on a blood flow, such as vascular blood flow, and/or volume characteristics from measuring on a thoracic bone or around the thorax and in the sternum bone of a subject. The method comprising providing 50 adapted to be arranged at a skin site of the thoracic bone or septum of a subject. The sensor includes at least one light source and at least one detector. One example of a suitable sensor is a sensor in accordance with the present disclosure. The method further comprises transmitting 21 light from the at least one light source to the thoracic bone or septum. Detecting 52 part of the light reflected and/or scattered back from the vessels in the bone using the detector. Recording 53 measured data related to the detected light and analyzing 54 the measured data from the detected and recorded light to obtain at least one physiological parameter.

Figure 6:
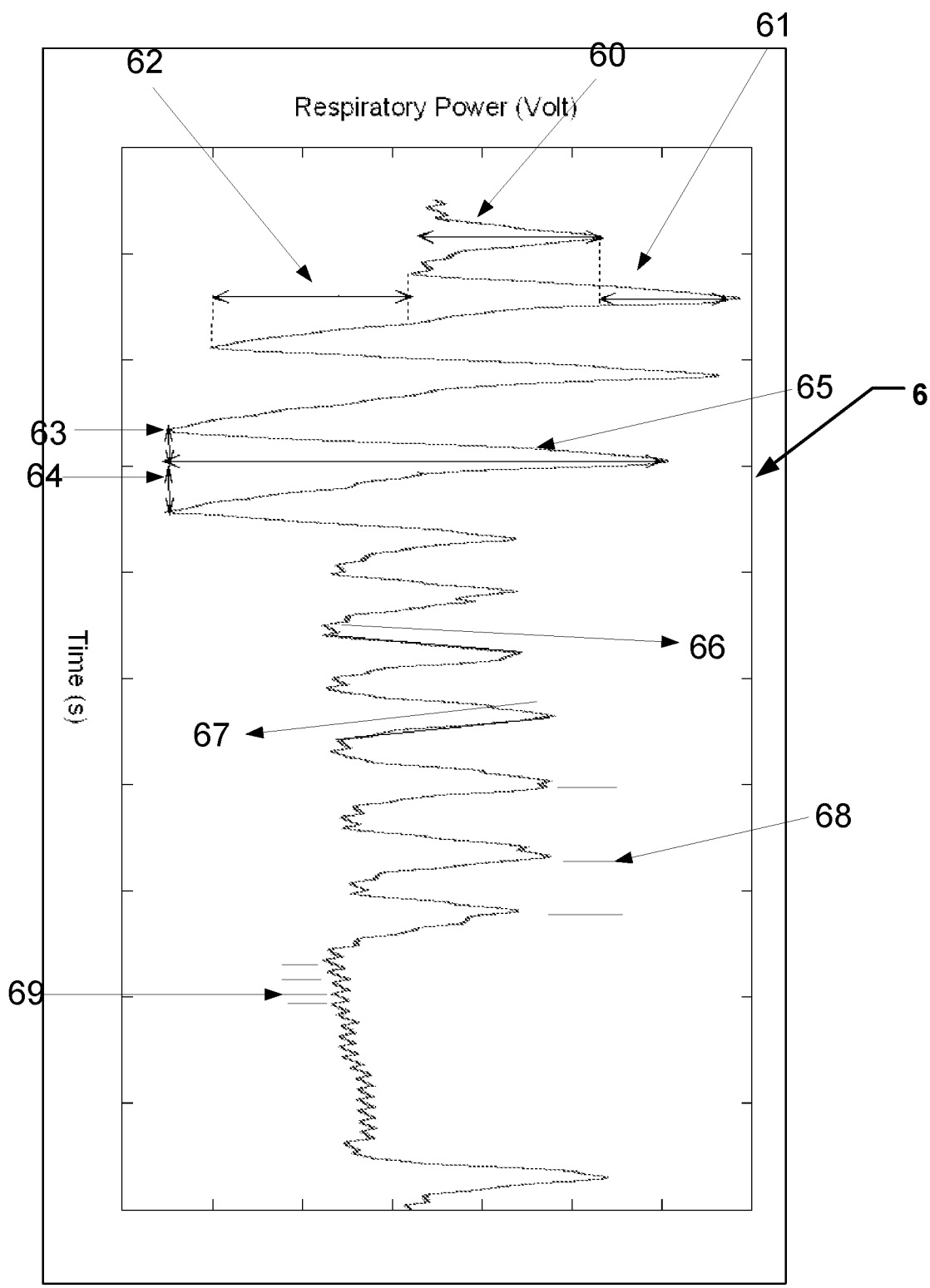
FIG. 6 is illustrating an arbitrary exemplary respiratory power curve recording from sternum of a healthy subject for illustrating purpose.

FIG. 6 is illustrating an arbitrary exemplary respiratory power curve 6 for illustrating purpose. The Respiratory Power (RP) curve 6 is obtained by a photoplethysmographic recording from the sternum on a healthy subject. Upward deflection indicates inspiration and downward deflection indicates expiration.

From the RP curve 6 in FIG. 6 several respiratory related parameters may be extracted:

68. Respiratory Rate (breaths/min) by count of peaks in the RP curve (preferable after LP filtering).
63. Inspiration time (s).
64. Expiration time (s).
60. Amplitude (V) during normal respiration describes the respiratory efficiency during normal breathing. Similarity with tidal volume (TV) or respiratory depth.
65. Maximal amplitude (V) during slow (not forced) maximal inspiration followed by slow maximal expiration describes the respiratory efficiency during maximal effort. Normalized by division with amplitude Similarity with vital capacity (VC).
61. Inspiratory reserve (V) during maximal inspiration. Normalized by division with amplitude.
62. Expiratory reserve (V) during maximal expiration. Normalized by division with amplitude.
66. Inspiration coefficient=($\Delta$RP/$\Delta$t); describes during inspiration a) the respiratory resistance due to obstruction and/or b) the extent of respiratory activity/ability.
67. Expiration coefficient=($\Delta$RP/$\Delta$t); describes during expiration a) the respiratory resistance due to obstruction and/or b) the extent of respiratory activity/ability.
69. Additionally, the heart rate (beats/min) may be determined by count of heart synchronous peaks (after high pass filtering of the RP curve in FIG. 6).

Additionally the Respiratory curve or pattern may be observed.

Additionally, oxygen saturation $SaO_2$ (%) may be determined according to the technique described above. The oxygen content is determined by a quotient between total (DC) light reflection and/or scattering of two wavelengths, for example 804 and 660 nm and/or 940 nm and 804 nm. This quotient has empirically been found to correspond to oxygen saturation in blood samples whereas oxygen saturation was measured at a chemical lab using standard lab methods. Due to total light reflection and/or scattering and the highly perfused sternum bone with steady metabolic need the determined oxygen saturation is assumed to be of arterial origin, which is denoted as $SaO_2$.

More respiratory parameters may be extracted from the RP curve when the subject/patient performs e.g. forced inspiration and expiration during 1 s, $FEV_1$.

It has earlier has been possible to monitor the Respiratory Rate (breaths/min) and Respiratory curve or pattern using PPG on soft tissue. However, the respiratory curve is much more evident and of higher signal strength when recorded on thoracic bone or sternum compared to recordings on soft tissue. Hence, the calculation of the respiratory frequency is highly facilitated technically when extracted from recordings on the sternum.

Apart from the Respiratory Rate (breaths/min) and Respiratory curve or pattern it has not been possible until now to monitor any of the other parameters using PPG on soft tissue because it is only on the thoracic bone or sternum bone that the respiratory signal is evident with enough high S/N (signal to noise ratio) due to the special anatomical vessel architecture, vessel branching and high blood delivery to the thorax compartments. This is partly due to the production of cells in the red bone marrow in the sternum and also the need of blood to the intercostal and abdominal muscles engaged in the respiratory activity and the vicinity to the heart and bigger vessels. Further parameters are the curve shape of the heart beat which is visible in the measured curves due to the short distance between the heart and the sternum.

From the measured physiological parameters it may be possible to indirectly determine if a patient has hyperthermia or hypothermia and the grades thereof.

Figure 7:
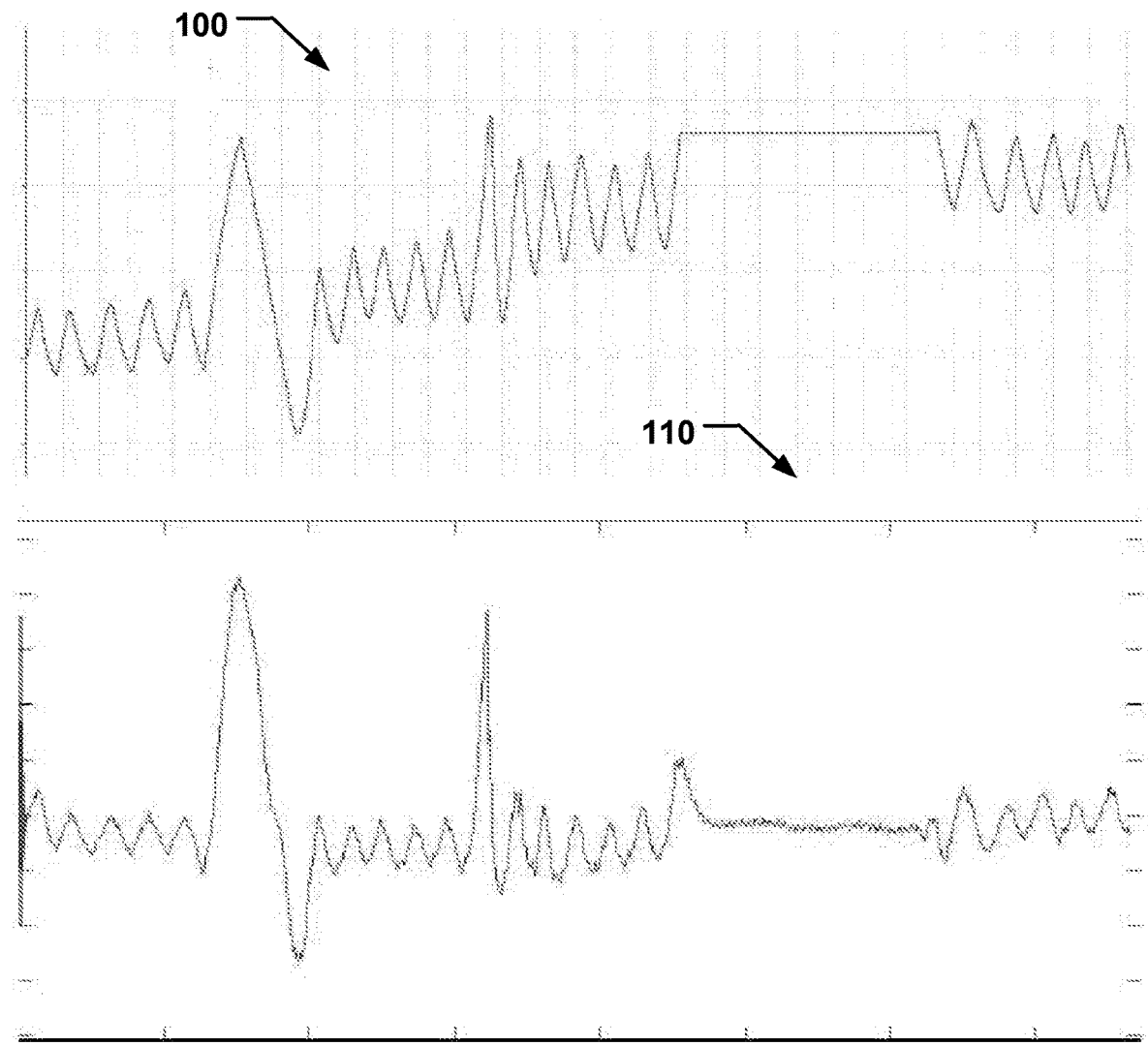
FIG. 7 is illustrating respiratory Power curve recording from sternum on a healthy subject compared with simultaneous spirometry recording in the airway.

FIG. 7 illustrates simultaneous recordings using the herein disclosed system and method 110 (lower curve) and a spirometer 100 (reflects air volumes) in a healthy subject during rest, maximal inspiration (upward deflection) and expiration (downward reflection) and during breath holding. The Respiratory Power Curve 110 follows the spirometry curve 100 at all phases and the respiratory rates also coincide.

Figure 8:
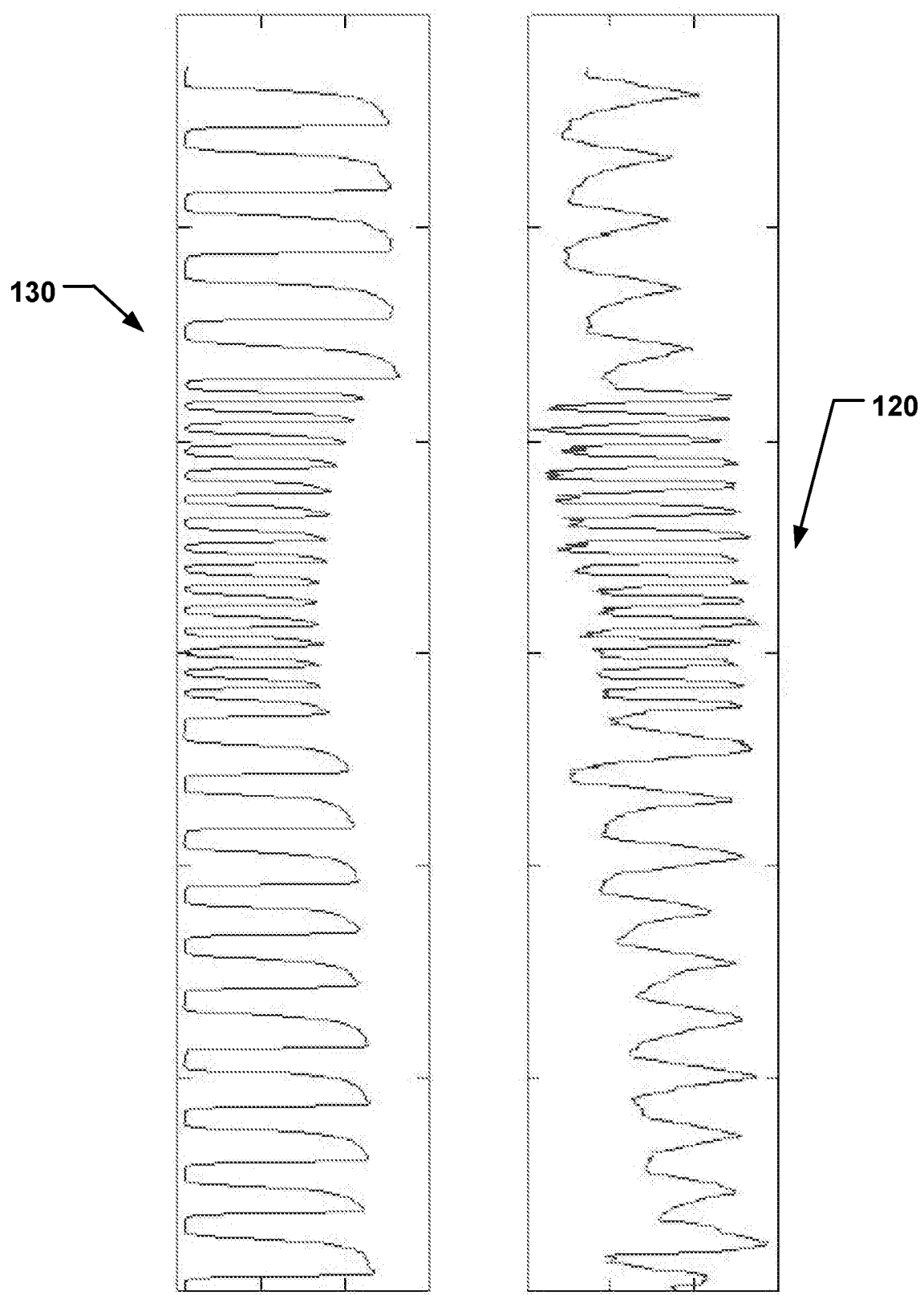
FIG. 8 is illustrating respiratory Power curve recording from sternum on a healthy subject compared with a simultaneous capnography recording in the airway.

FIG. 8 illustrates simultaneous recordings using the herein disclosed system and method 120 (upper curve) and a capnograph 130 (lower curve) on a healthy subject in rest and during hyperventilation (increased respiratory rate). The Respiratory Power Curve 120 is obtained by recordings from the sternum on a healthy subject. The recording of the capnograph 130 is obtained from the airways and reflects variations in $CO_2$ concentration during inspiration and expiration and as seen there is a high resemblance in respiratory rate comparing the methods.

Figure 9:
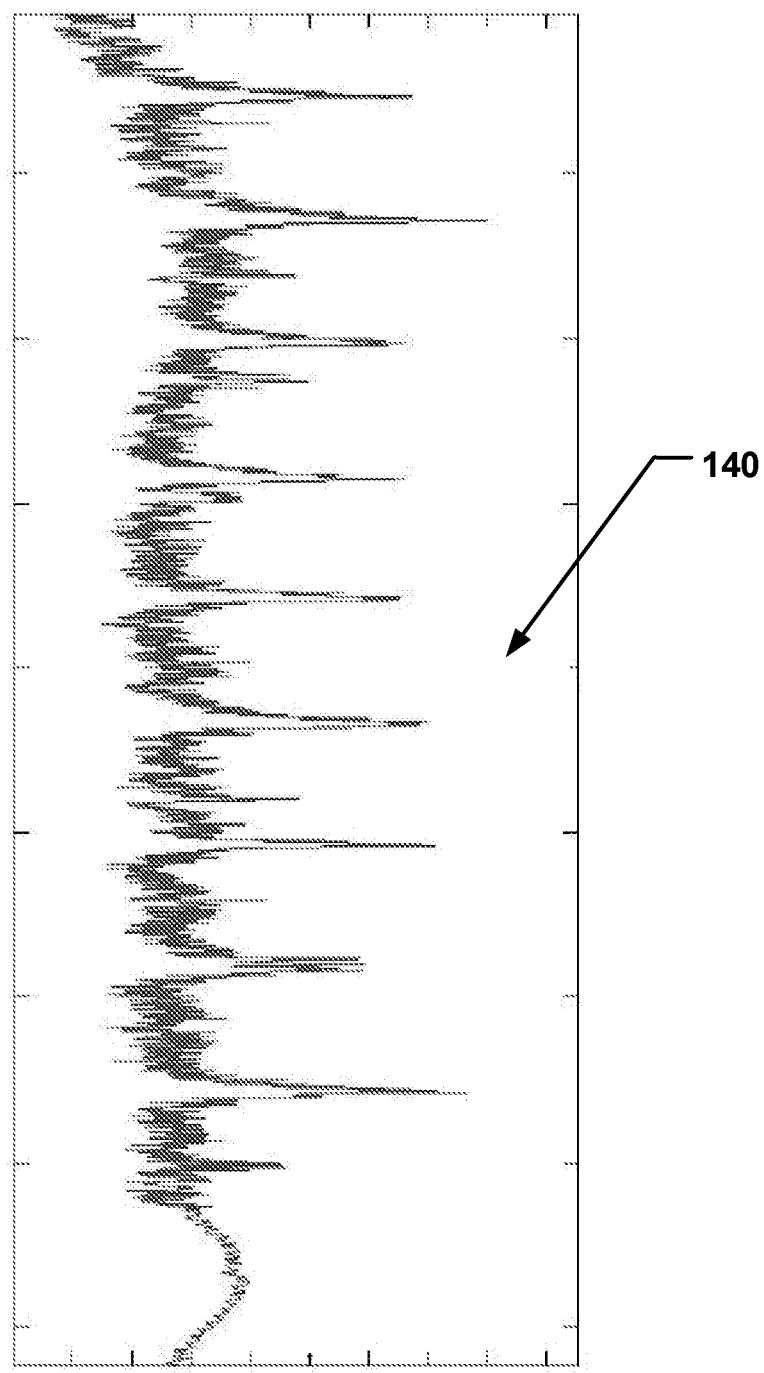
FIG. 9 is illustrating respiratory Power curve recording from sternum on a chronic obstructive pulmonary disease (COPD) patient during a walking test.

FIG. 9 illustrates a Respiratory Power Curve 140 recording using the herein disclosed system and method on a female patient with COPD during a 6 minutes walking test. The Respiratory Power Curve shows deep sighs in order to be able to perform the walking procedure. This particularly demonstrates the possibility to follow and reflect the respiratory pattern on patients with different dysfunctional breathing when utilizing the herein disclosed system and method.

Figure 10:
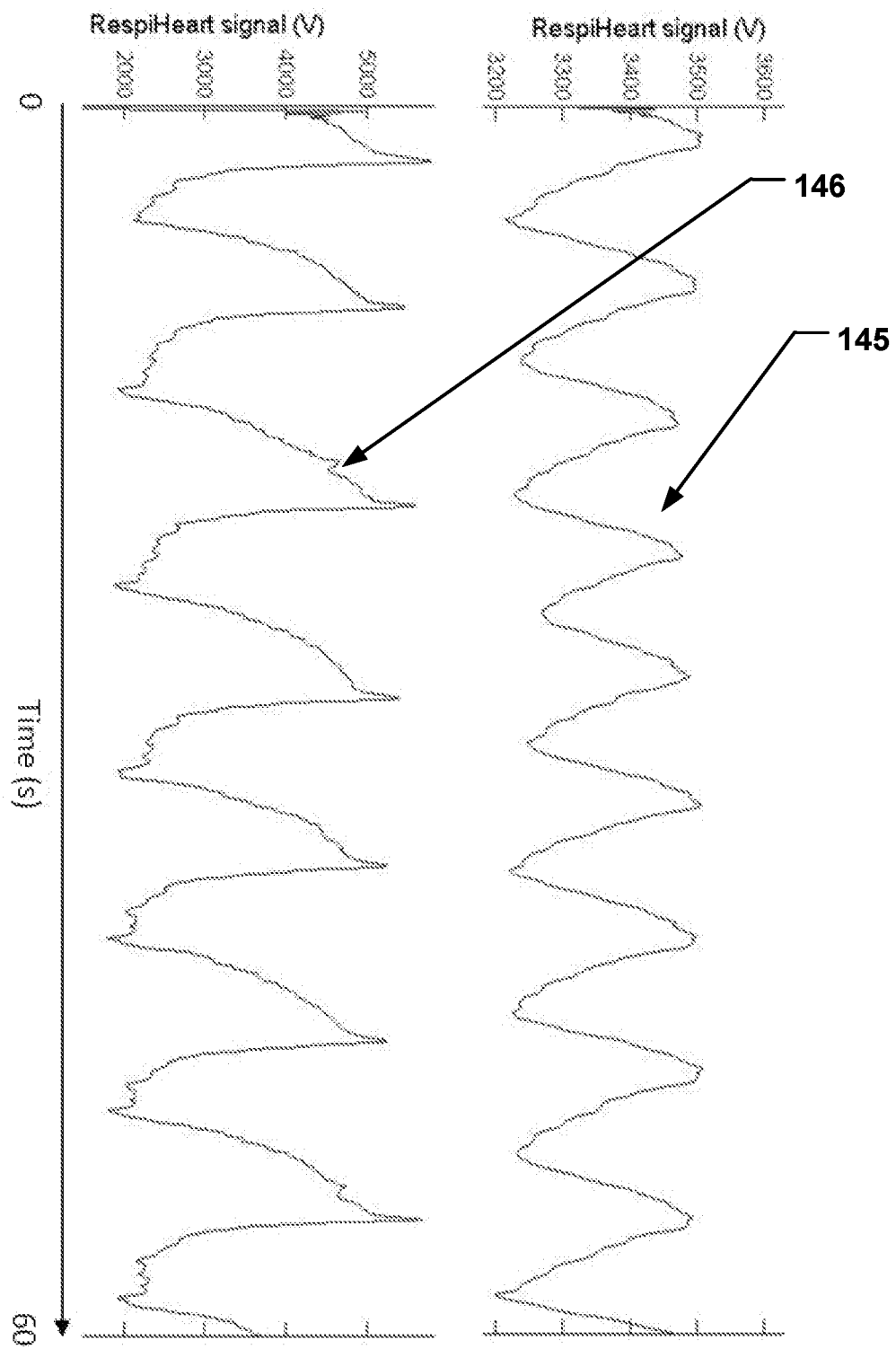
FIG. 10 is illustrating respiratory capacity and respiratory pattern of a patient with cystic fibrosis before and after exercise.

FIG. 10 illustrates recordings using the herein disclosed system and method on a patient with cystic fibrosis. The patient performed respiratory physical exercise, expiratory resistance breathing and inhalation of drugs in order to evacuate phlegm and mucus during 45 min. FIG. 10 illustrates the respiratory capacity and respiratory pattern before (145) and after the exercise (146). As can be seen the peak-to-peak value (corresponding to respiratory volume) measured by RespiHeart (V) increased 10 fold after the exercise, from a peak-to-peak value of 300 before (145) to a peak-to-peak value of 3000 after (146) exercise. There was also a change in respiratory pattern indicating the ease to inspire more air (according to patient's statement) after the exercise.

Figure 11:
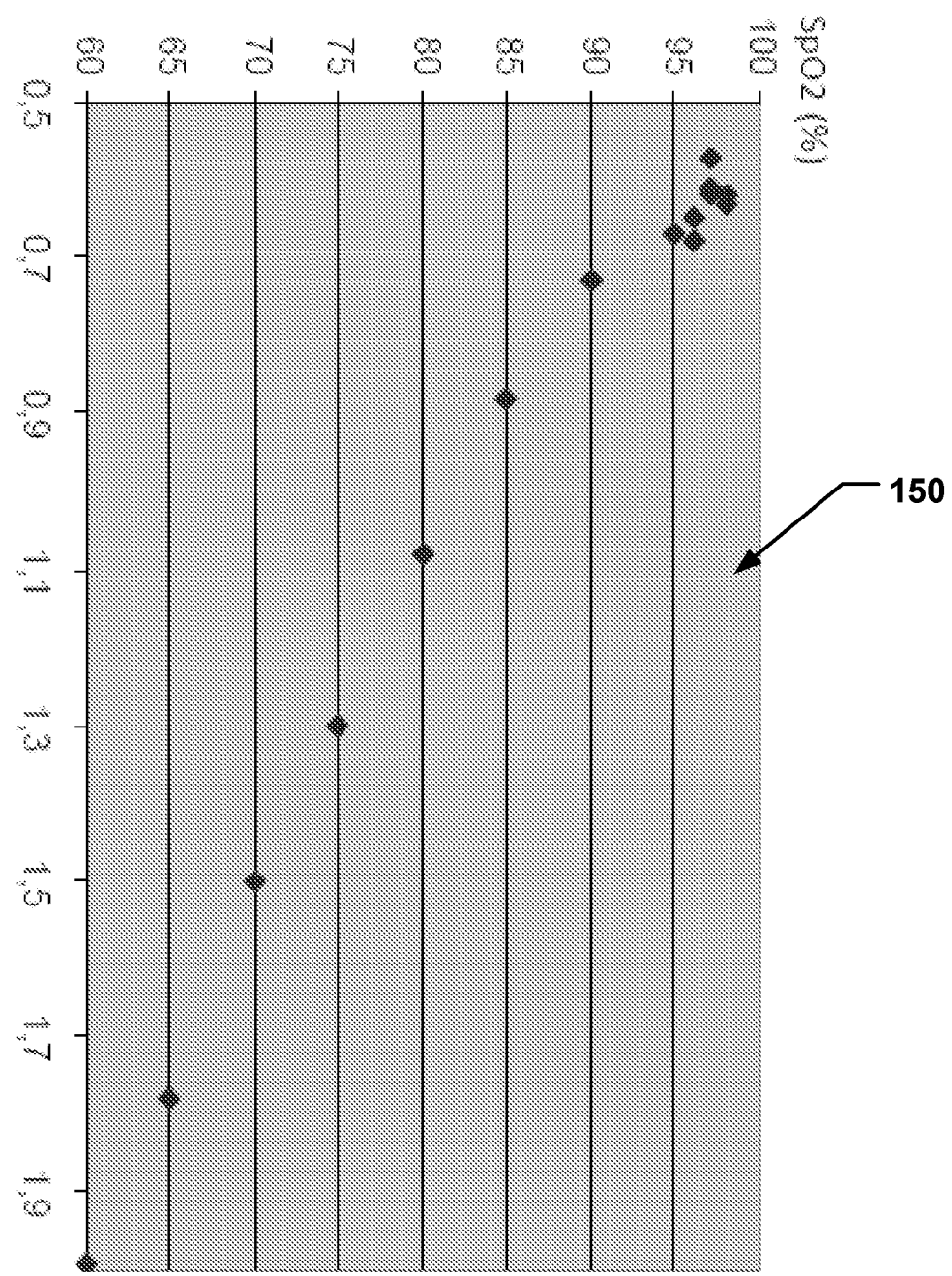
FIG. 11 is illustrating quotient during voluntary breath holding.

FIG. 11 illustrates the quotient 150 between total (DC) light reflection and/or scattering of two wavelengths at 804 and 660 nm determined from a recording with the herein disclosed system and method and plotted against oxygen saturation measured by a pulse oximeter (Allen J 2007 Photoplethysmography and its application in clinical physiological measurement. Physiol. Meas. 28:R1-R39) during breath holding on one free diver (lying position). The example demonstrates the ability of the disclosed system and method to follow variations in oxygen saturation.

Figure 12:
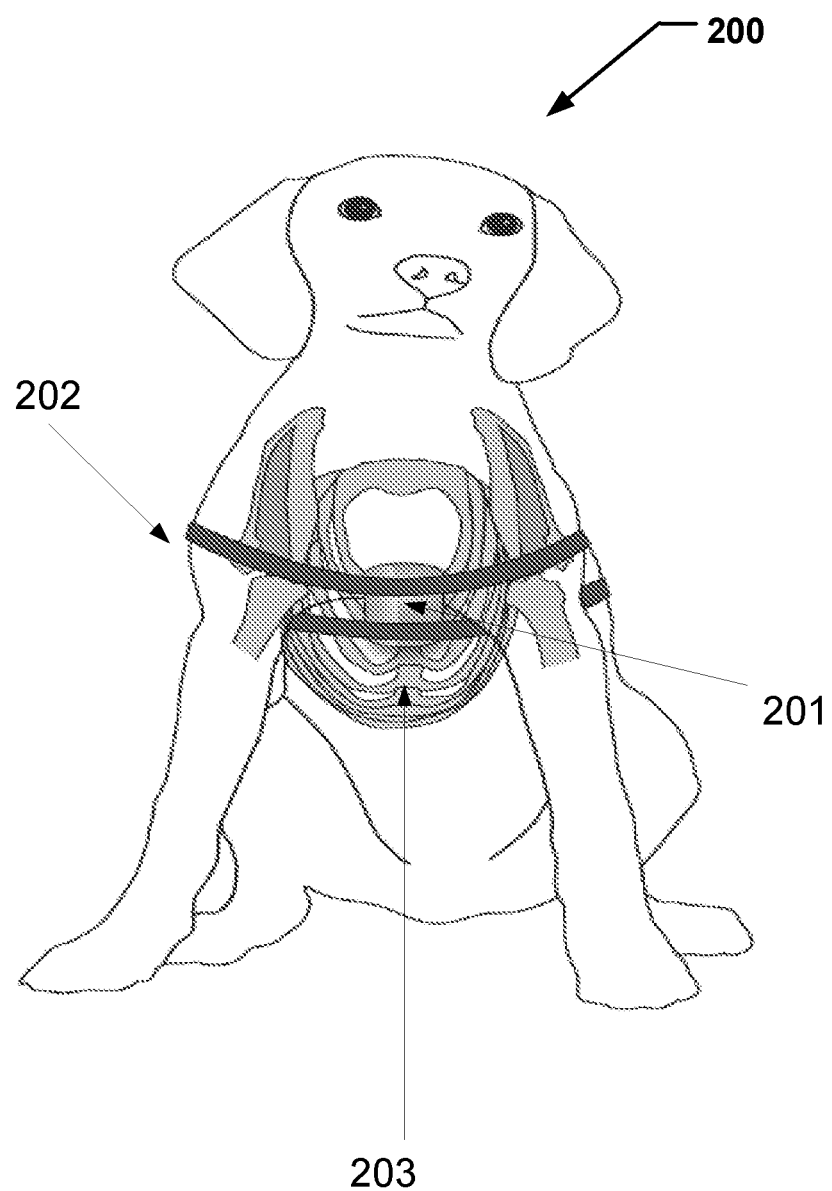
FIG. 12 is illustrating examples of devices in accordance with the disclosure and positions at an animal apposition to a thoracic bone or sternum.

FIG. 12 is illustrating examples of systems 201 in accordance with the disclosure and positions at an animal 200 apposition to a thoracic bone or sternum 203. In this example the system 201 is fastened means 202. The fastening means 202 could be as straps, such as ratchet straps or elastic straps. The sensor of the system may be positioned in the fur or the animal 200 may be locally shaved to obtain a spot where the sensor of the system 201 may be positioned directly on to the skin of the animal 200.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A method for non-invasively determining at least one physiological parameter based on a vascular blood flow and/or volume in a thoracic bone or a sternum of a subject, said method comprising:
    providing a sensor comprising at least one light source and at least one detector adapted to be arranged at a skin site of said thoracic bone or said sternum of said subject,
    wherein said at least one light source comprises two near-infra-red LEDs having a wavelength in the range of 800 to 810 nm, and two red LEDs having a wavelength in the range of 640 to 680 nm, and said at least one light detector comprises four photodetectors,
    said LEDs and said photodetectors arranged in a double lining configuration covering vessels emerging from left and right internal thoracic arteries and its corresponding collecting veins,
    wherein a length of said sensor correlates to a volume of blood covered during a measurement, and wherein an optical geometry of the LEDs and photodetectors is arranged so that the light can penetrate and reach the vessels in the thoracic bone or in the sternum bone;
    transmitting light from said at least one light source to said thoracic bone or sternum;
    detecting at least a part of said transmitted light being reflected and/or scattered by blood vessels in said thoracic bone or said sternum;
    analyzing and evaluating said reflected and/or scattered light detected by said at least one detector for determining said at least one physiological parameter;
    wherein the at least one physiological parameter comprises oxygen saturation SaO2 (%) in the sternum bone, which is determined by a quotient between total Direct Current (DC) light reflection or scattering of said near-infra-red wavelength and said red wavelength.

2. The method according to claim 1, comprising assessing blood flow in rigid vessels or in vessels of limited flexibility.

3. The method according claim 2, wherein said analyzing and evaluating is assessed from the blood flow supply anatomy of the sternum, wherein
    said blood flow to sternum varies synchronously with said blood flow supply to other parts of sternum.

4. The method according to claim 1, wherein said at least one physiological parameter further comprises any of Respiratory Rate, Inspiration time, Expiration time, respiratory efficiency during normal effort, respiratory efficiency during maximal effort, Inspiratory reserve, Expiratory reserve, Inspiration coefficient, Expiration coefficient, heart rate (beats/min), Respiratory curve or pattern, hemoglobin content or temperature.

5. The method according to claim 1, comprising monitoring said at least one physiological parameter in real-time.

6. The method according to claim 1, wherein said light source further comprises at least one green light source.

7. The method according to claim 6, wherein said green light source has as a wavelength between 540 nm to 590 nm.

8. The method according to claim 6, wherein a hemoglobin content is determined by a quotient between a total of reflected and/or scattered light of said green light and a total of reflected and/or scattered light of said near infrared light.

9. The method according to claim 6, wherein said near infrared light source wavelength in the range of 800 nm to 810 nm is used as a reference.

10. The method according to claim 1, wherein the step of analyzing and evaluating said reflected and/or scattered light detected by said at least one detector for determining said at least one physiological parameter comprises recording a respiratory power (RP) curve for a subject during inspiration/expiration for a period of time (t).

11. The method according to claim 10, wherein the at least one physiological parameter comprises an inspiration coefficient which is calculated from the formula $\Delta RP/\Delta t$ during a period of inspiration.

12. The method according to claim 10, wherein the at least one physiological parameter comprises an expiration coefficient which is calculated from the formula $\Delta RP/\Delta t$ during a period of expiration.

* * * * *